(12) United States Patent
Leahy et al.

(10) Patent No.: US 6,429,194 B1
(45) Date of Patent: *Aug. 6, 2002

(54) MUCIN CONTAINING OPHTHALMIC PREPARATION

(75) Inventors: Charles D. Leahy, Concord; Edward J. Ellis; Jeanne Y. Ellis, both of Lynnfield, all of MA (US)

(73) Assignee: Vista Scientific LLC, Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/888,144

(22) Filed: Jun. 22, 2001

Related U.S. Application Data

(63) Continuation of application No. PCT/US01/19625, filed on Jun. 18, 2001, and a continuation-in-part of application No. 09/829,405, filed on Apr. 9, 2001, which is a continuation of application No. 09/598,089, filed on Jun. 21, 2000, now Pat. No. 6,248,360, application No. 09/888,114, which is a continuation-in-part of application No. 09/516,671, filed on Mar. 1, 2000, now Pat. No. 6,281,192.

(60) Provisional application No. 60/283,976, filed on Apr. 16, 2001, and provisional application No. 60/122,073, filed on Mar. 1, 1999.

(51) Int. Cl.$^7$ ............................................... A61K 38/16
(52) U.S. Cl. ............................................ 514/8; 514/912
(58) Field of Search ...................................... 514/8, 912

(56) References Cited

U.S. PATENT DOCUMENTS 4,287,175 A * 9/1981 Katz
4,914,088 A * 4/1990 Glonek et al.

* cited by examiner

Primary Examiner—Zohreh Fay
(74) Attorney, Agent, or Firm—Cantor Colburn LLP

(57) ABSTRACT

Aqueous ophthalmic preparations are provided and are intended to be instilled into the eye, or in which to pre soak or store an object to be inserted into the eye, such as a contact lens, an ointment, or a solid device to be inserted into the conjunctival sac. The preparations disclosed are utilized for the treatment of a tear film and ocular surface disorder known as keratoconjunctivitis sicca or dry eye syndrome. In general, the preparations of this invention are also effective for the relief of symptoms of eye irritation, such as those caused by dry environmental conditions or by contact lens wear. In accordance with the present invention, the ophthalmic preparation includes a mucin component, similar to that found at the normal human ocular surface and in one exemplary and preferred embodiment, the mucin is a transmembrane or surface mucin.

32 Claims, No Drawings

MUCIN CONTAINING OPHTHALMIC PREPARATION

CROSS REFERENCE TO RELATED APPLICATIONS

This application is a continuation-in-part of U.S. Ser. No. 09/829,405, filed Apr. 9, 2001, which is a continuation of U.S. Ser. No. 09/598,089, filed Jun. 21, 2000 now U.S. Pat. No. 6,248,360. This application is also a continuation of International PCT Serial No. PCT/US01/19625, filed Jun. 18, 2001 (published in English), and claims the benefit of a previously filed Provisional Application No. 60/283,976, filed Apr. 16, 2001. The contents of these applications are incorporated herein by reference.

This is a continuation-in-part of U.S. patent application Ser. No. 09/516,671, filed Mar. 1, 2000, which claims the benefit of U.S. Provisional Patent Application No. 60/122,073, filed Mar. 1, 1999; both of which are incorporated herein by reference in their entirety.

This invention was made with government support under grant no. 1 R43 EY12573-01 awarded by the National Institutes of Health. The government has certain rights in the invention.

FIELD OF THE INVENTION

The present invention relates to ophthalmic preparations and more specifically relates to ophthalmic preparations for use as a tear film supplement, wherein the preparation comprises a mucin component.

BACKGROUND OF THE INVENTION

Initial descriptions and models of the tear film described the tear film as including three distinct layers and as being a three-layered, aqueous-dominated tear film. One of the layers comprises a mucin layer which serves primarily to render the hydrophobic ocular surface hydrophilic, so that the aqueous layer comprising the bulk of the tear film will spread evenly over the eye.

Current work in this field has shown that the classic aqueous-dominated tear film model has been replaced by the more probable concept of a mucin-dominated gel. This gel has its highest concentration of mucin at the epithelial surfaces of the cornea and conjunctiva, and the mucin concentration gradually decreases farther out into the tear film. In this model, the presence of mucin remains significant for the structure, stability and function of the entire tear film. Recent studies of the tear film using laser interferometry and confocal microscopy might be including the entire gel layer in indicating that the human tear film is 30 to 40 microns thick, more than four times thicker than earlier estimates.

Based on tear film physiology and clinical observations, tear film abnormalities are commonly designated by focus on a specific deficiency, such as an aqueous tear deficiency, keratoconjunctivitis sicca (KCS), a mucin deficiency, a lipid abnormality, an impaired lid function, or an epitheliopathy. Although clinically useful, the simplistic concept of a lack of one component of the tear film as the cause of dry eye has given way to a much more sophisticated view of ocular surface disease that involves: (1) the health and regulation of the various glands contributing secretions to the tear film, (2) changes in the tear film itself, such as in osmolality and content of inflammatory mediators, and (3) what is viewed as a sort of "final common pathway", the subsequent changes to the ocular surface. In fact, many clinicians and authors prefer the term "ocular surface disease" over "dry eye", for it is change to the ocular surface, whatever the original cause, that results in the significant signs and symptoms of dry eye. The discomfort of ocular surface disease is expressed in ocular symptoms, such as dryness, grittiness, burning, soreness or scratchiness, with variation among individuals. These symptoms can also be exacerbated by factors such as environmental conditions and contact lens wear. The combination of varying clinical signs and symptoms has also been termed dry eye syndrome.

Over the past twenty to thirty years many attempts have been made to provide an effective and long lasting treatment of dry eye symptoms, particularly for patients with moderate to severe KCS. These prior art attempts can be categorized on the basis of their physical state: ointments, emulsions, solid devices and aqueous based solutions or gels. Ointments are generally anhydrous preparations based on mixtures of white petrolatum and mineral oil. Because these formulations are greasy and cause blurred vision, they are not widely used other than in cases of severe symptoms, and are mostly limited to application at night just before sleeping. Emulsion based formulations for treating dry eye symptoms have emerged over the past ten years. One approach has been disclosed in a series of U.S. Pat. Nos. 5,578,586; 5,371,108; 5,294,607; 5,278,151; 4,914,088, all of which are herein incorporated by reference in their entirety. These patents teach the methods and compositions for reducing evaporation of the aqueous layer from the surface of the eye. The method comprises applying an admixture of a charged phospholipid and a non-polar oil over the eye, preferably in the form of a finely divided oil-in-water emulsion. Another approach is described in U.S. Pat. Nos. 4,818,537 and 4,804,539, incorporated herein by reference in their entirety, where liposome compositions in the form of emulsions are claimed to provide enhanced retention on ocular surfaces and thereby alleviate the symptoms of dry eye.

Solid devices, in the form of ocular inserts, have been utilized for longer term symptomatic relief of dry eye. These devices are placed in the eye and slowly dissolve or erode to provide a thickened tear film. Often patients find these devices difficult to insert and once in place, they tend to be uncomfortable. Examples of this technology are given in U.S. Pat. Nos. 5,518,732; 4,343,787, and 4,287,175, all of which are incorporated by reference in their entirety.

The most recommended and commercially successful methodology to treat dry eye symptoms is aqueous based solutions or gels. For the patient, eye drops are convenient and easy to apply relative to the other options mentioned above. There are at least thirty artificial tear products currently on the market from which to choose. For the most part the "active" ingredients in these present day artificial tear formulations are common water soluble or dispersable polymers such as: hydroxyethylcellulose; hydroxypropylmethylcellulose; methylcellulose; carboxymethylcellulose; polyvinyl alcohol; polyvinyl pyrrolidone; polyethylene glycol; carbomers; and poloxamers.

These currently marketed products, while providing temporary relief of symptoms—usually measured in minutes—are strictly palliative without long term effect. In fact, to truly maintain relief of symptoms in moderate to severe cases, an impractical schedule of doses would be necessary. With preserved solutions, the frequency of instillation can lead to signs and symptoms of irritation, making it necessary to utilize expensive and more cumbersome unit dose delivery packages.

The recent patent literature indicates a continued interest in pursuing synthetic based artificial tear solutions. For example, U.S. Pat. No. 5,460,834, incorporated herein by reference in its entirety, teaches the use of hydroxypropylmethylcellulose along with other ingredients as an ophthalmic solution, and PCT publication WO98/11875, incorporated herein by reference in its entirety, discloses the use of polyvinylpyrrolidone in combination with other components to relieve eye dryness.

The art recognizes that an ophthalmic solution must provide an effective and long lasting treatment for symptoms of dry eye. One approach to achieving these aims is to provide a solution with tailored rheological properties, that is, a high viscosity solution that yields or flows under stress. Examples of this approach are disclosed in U.S. Pat. Nos. 5,075,104 and 5,209,927, incorporated herein by reference in their entirety, where the rheological properties of the ophthalmic solutions are attained through the use of carbomer polymers. These carbomer polymers have been found to be bio-adhesive as described in U.S. Pat. Nos. 5,225,196; 5,188,828; 4,983,392 and 4,615,697, all of which are incorporated by reference in their entirety. It is believed that the bio-adhesive properties of the carbomer contributes to longer retention times in the eye. In fact, U.S. Pat. Nos. 5,075,104 and 5,209,927, incorporated by reference in their entirety, teach "that the carbomer polymers appear to function by maintaining or restoring the normal hydration equilibrium of the epithelial cells, protecting the cornea in a manner similar to that believed to be provided by the mucin component of normal tears. Therefore, in theory, the polymers, in addition to being well retained in the eye and providing lubrication, can function as a mucin substitute in the dry eye syndrome where there is a deficiency or absence of the natural mucin component of the normal tears".

Polymers that exhibit mucin-like properties are often referred to as "mucomimetic". Usually in the art the mucin-like property provided by such "mucomimetic" polymers is simply viscosity. While it is true that a viscous solution will stay in the eye somewhat longer, it is the viscoelasticity, rather than simply the viscosity, of the gel-forming mucin of the tear film that is critical to its protective function during blinking. Additional lubrication and protection from drying and physical trauma to the ocular surface itself comes from the transmembrane mucin expressed on the surface of the entire ocular surface epithelium. It has also been proposed that this transmembrane mucin plays a critical role in spreading and maintaining the tear film structure through its interaction with the secreted gel-forming mucins of the tear film.

Mucins are the most important component in the tear film for promoting lubrication during the blinking process. The rate of shear during blinking can be very high. At such levels damage to cells and subsequent pain will occur if the shearing forces generated during blinking are transmitted to the epithelial surfaces. Two rheological conditions can mitigate the action of the shearing forces due to blinking. Firstly, shear thinning (non Newtonian behavior) of the tear film as the shear forces increase will result in a reduction of the apparent viscosity. Secondly, the energy associated with the shear forces can be partially absorbed by the elastic component of the tear film. These rheological conditions are provided by the viscoelastic properties of ocular mucin secretions, both in the gradient concentration of the fluid layer and in the gel near the epithelial surface. As a result, during eye movement the mucin can act on the stress gradient across the tear film and reduce the shear forces to near zero at the cell surfaces. Current commercial artificial tear products do not achieve the viscoelastic properties of human tears and have very limited retention time and lubricity effect in the eye.

The search for mucin-like polymers has extended into the area of bio polymers, with particular emphasis on the naturally occurring polysaccharides. One polymer, hyaluronic acid, and its sodium salt have received much attention over the past several years. In fact, one commercial product, Hylashield®, based on a high molecular weight sodium hyaluronate, has been successfully marketed as a dry eye treatment solution. The use of hyaluronic acid in artificial tear solution compositions is also taught in U.S. Pat. Nos. 5,470,628; 5,460,834 and 5,106,615, all of which are incorporated by reference in their entirety. Other polysaccharides, such as carrageenan, tamarind gum and keratan sulfate have been claimed to have utility in artificial tear solutions as disclosed in U.S. Pat. Nos. 5,403,841 and 5,460,834 and PCT publications WO97/28787, all of which are incorporated by reference in their entirety. In addition, polysaccharides, such as alginate, dextran, scleroglucan and xanthan have been used, or have been proposed for use in ophthalmic solutions.

Prior art clearly recognizes the importance of mucin in the natural tear fluid as a wetting agent, viscoelastic gel former, lubricant and barrier to bacterial adhesion. Limited success with so many various synthetic and substitute polymers indicate that supplementing the tear fluid with a compatible mucin from an exogenous source would appear to be a more direct and preferred method for addressing dry eye conditions. Part of the problem in the development of ocular surface changes in dry eye disease may be the dehydration of the mucus gel and subsequently the mucin layer of the cellular surface. Supplementing the tear fluid with mucin in an aqueous solution would be expected to help maintain the natural surface mucin layer of the eye by both the addition of the additional mucin molecules and the hydration provided by the aqueous vehicle.

Perhaps one reason that mucin-based ophthalmic solutions have not been developed is the limited commercial availability of mucin. The mucins that are available are partially purified from bovine submaxillary glands, or from porcine guts. These by-products of the meat packing industry are distributed by Sigma Chemical Company (St. Louis, Mo.) and Worthington Biochemical Corp. (Freehold, N.J.). The most notable problem with currently available commercial mucins is their very poor quality. For example, fractionation of BSM mucin from Sigma by SDS-PAGE reveals that the preparation is heavily contaminated by low molecular weight proteins that are either degraded mucin, or proteins unrelated to mucin.

The patent literature reveals one reference to the use of mucin in sterilized, preserved and stable solutions. U.S. Pat. No. 4,438,100, incorporated by reference in its entirety, describes mucin-containing solutions for application to sensitive mucous membranes of the oral cavity, the nasal system and the eye. The mucins utilized in this invention are non human mammalian mucins selected from the group consisting of buccal and gastrointestinal mucins. In fact, the source of their mucins is mucus, a mature and complex secretion containing a mixture of various mucin molecules as well as other proteins and associated contaminants of secretion. The is no distinction made between secreted mucins and mucins expressed by the surface cells of the oral cavity or gastrointestinal mucous membranes. The inventors provide examples of mucin-containing solutions for use as artificial saliva, but do not teach the preparation of ophthalmic solutions. In fact, the inventors discuss the potential use of mucin-containing ophthalmic solutions in conjunction with contact lens care. It is evident that the inventors did not contemplate the use of mucin as a tear supplement.

SUMMARY OF THE INVENTION

The present application is directed to ophthalmic preparations for use as a tear film supplement. More specifically, this application relates to an aqueous formulation to be instilled into the eye, or in which to pre soak or store an object to be inserted into the eye, such as a contact lens, an ointment, or a solid device to be inserted into the conjunctival sac. The preparations disclosed are utilized for the treatment of disorders such as keratoconjunctivitis sicca or dry eye syndrome. In general, the preparations are also effective for the relief of symptoms of eye irritation, such as those caused by dry environmental conditions or by contact lens wear.

In particular, the present application relates to ophthalmic compositions comprising a mucin component, similar to that found at the normal human ocular surface, as well as to methods for their preparation and storage. The application also relates to a method of treating the eye by topically applying the composition of the present invention, when indicated, to provide lubrication and protection of the ocular surface, for the relief of dryness and discomfort symptoms, such as experienced in patients with dry eye and following traumatic injury or surgery, and when indicated to achieve the other effects mentioned above. In one preferred embodiment the compositions of the present invention are provided as buffered, sterile aqueous solutions. The subject compositions may be unpreserved (provided in a unit dose format) or may be preserved.

In one embodiment, the mucin component is a transmembrane or surface mucin (e.g., those mucins classified as MUC1 or MUC4) and is expressed at the epithelial surface of various mucosal, glandular and ductal organs and tissues in mammals. Such organs and tissue include the ocular surface, mammary glands, salivary glands, esophageal epithelium, stomach, pancreas, bile ducts, lung epithelium, kidneys, bladder, and the uterus. Mucous membranes are found in the bucal and nasal cavity surfaces as well as the gastrointestinal, tracheobronchial and reproductive tracts. As a result of its expression in the mammary gland epithelium of mammals, MUC1 is a surface component of the fat globules in secreted mammalian milk. To form the exemplary ophthalmic preparations disclosed herein, other ingredients commonly employed in ophthalmic formulations are utilized to provide a balance of physiologically acceptable properties, depending on whether the final product is a solution, ointment, gel or solid.

The above-discussed and other features and advantages of the present invention will be appreciated and understood by those skilled in the art from the following detailed description.

DETAILED DESCRIPTION OF THE PREFERRED EMBODIMENTS

Mucins refer to a family of glycoproteins of high molecular weight, secreted or expressed by goblet and nongoblet epithelial cells of mucosal tissues. These mucins predominate in the formation of mucus, a highly hydrated gel of particular structure and function. Mucins are heavily glycosylated high molecular weight glycoproteins with predominantly O-linked oligosaccharide side chains. Mucin molecules are generally above 200 Kda, with carbohydrate composing 50% or more of their dry weight. At least nine distinct mucin genes have been identified (MUC1, 2, 3, 4, MUC5AC, MUC5B, MUC6, 7 and 8). Furthermore, each of these is produced in various forms in different tissues. This suggests that the mucins serve unique, tissue-specific protective functions at the apical surfaces of specialized epithelial cells. MUC1, the so-called "epithelial mucin", is a membrane-spanning mucin found in abundance in epithelial tissues. MUC1 is known by various other names, such as polymorphic epithelial mucin or episialin. MUC1 has a molecular weight in the 125 to 225 KDa range, which is low when compared to the other types of mucin.

In the human eye, the secretory mucins MUC2 and MUC5AC have been detected (via transcripts at the nucleic acid level) from conjunctival isolates, and only MUC5AC has been localized to conjunctival goblet cells. The transmembrane mucin MUC1 is associated with the cell membranes of the entire corneal and conjunctival epithelial surface, except the goblet cells. Another transmembrane mucin is the mucin MUC4, which is associated with the cell membranes of the entire conjunctival epithelial surface, except the goblet cells. Qualitative and quantitative analyses of ocular mucins are difficult because there are as yet no specific probes for individual ocular mucins, and little is known about the mechanisms or extent of synthesis or secretory regulation of these mucins. One or more calcium dependent processes are possible, with involvement of several secretagogues, such as prostanoids, autonomic transmitters, and neuropeptides being investigated.

The secreted ocular mucins are relatively large molecules, and have a significant role in the gel-forming nature of the tear film. The model of the greater part of the tear film being a highly hydrated mucus gel, rather than simply a watery aqueous layer, is becoming increasingly accepted. The viscoelasticity of the tear film derives from the specific structure and gel-forming properties of the ocular mucins, and allows the tear film to absorb the shear force of the blink, which would otherwise irritate and damage the ocular surface. The transmembrane mucin, on the other hand, serves more as a protective layer on the actual cellular surface of the ocular epithelium, functioning to directly protect and lubricate the ocular surface, as well as to anchor the highly hydrated gel (mucus) of the tear film gel-forming mucins, thereby assisting in the spreading and stability of the tear film over the ocular surface.

Stratified layers of the above mucins are known to form over the surface of mucosal membranes, such as in the gut, affecting the flow and interaction of the protective layer and its contents with the cellular surface of the epithelium. A difficiency in one type of mucin would therefore be expected to affect the lubricating, protective, barrier and other functions of the other mucins at the mucosal surface.

In a mild to moderate dry eye, the goblet cell density is not significantly reduced, indicating that MUC5AC is most likely still able to be produced normally, in quantities sufficient to be spread over the entire ocular surface. However, localized early ocular surface changes resulting from dryness, such as that revealed by fluorescein or rose bengal staining, can be seen in the epithelia of the corneal and conjunctival surfaces. This localized damage to the ocular surface indicates that even marginal dryness might have a significant effect on the presence of functional MUC1 on the surface of the ocular epithelium. Since one of the proposed functions of MUC1 is to help the other, more abundant gel-forming ocular mucins adhere to the ocular surface, a paucity of MUC1 might significantly affect the stability of the tear film, even in the presence of an abundance of MUC5AC secreted by the conjunctival goblet cells. When investigated using the technique of impression cytology, the more severe ocular surface changes resulting from dryness, exhibited in the process of squamous metaplasia, are also seen to occur initially in localized areas.

These more pathological localized surface changes are further evidence for a critical protective role of MUC 1. There is some early evidence that with the progression of changes to the ocular surface mucins associated with dry eye, as detected by immunohistochemical methods, the goblet cells themselves try to make up for the lack of normal expression of MUC1 by the rest (non goblet cells) of the corneal and conjunctival surface epithelium, and begin expressing a MUC1-like molecule in their secretions.

Although not being held to any one theory we believe that the particular type of mucin described in this invention, being a transmembrane or surface mucin, acts to protect and lubricate the ocular surface, as in the role of the natural transmembrane mucins, MUC1 and MUC4, which is expressed by the entire surface epithelium of the conjunctiva and cornea. By supplementing the natural epithelial surface mucin, the lubrication and protection of the ocular surface is enhanced, in order to slow the progression, and associated development of symptoms, of changes to the ocular surface epithelium, such as decreased tear film stability, increased staining with fluorescein sodium or rose bengal, decreased goblet cell density and the development of squamous metaplasia seen with ocular surface disease. The property of viscosity in the preferred embodiment is primarily targeted to assist in retention of the invention in the eye at the ocular surface, as well as for lubrication and comfort associated with instillation. Viscosity is not the physical property which gives the mucin formulation of this invention its "mucomimetic" function. This invention primarily protects and lubricates the ocular surface and interacts with the gel-forming secreted mucins of the tear film, thereby enhancing the spreading of the tear film, and by default of instillation adds to the tear film volume and hydration of the ocular surface. The "mucomimetic" effects of this invention, therefore, are those of the transmembrane mucin expressed on the ocular surface epithelium, and not the gel-forming mucins secreted by the goblet cells. Together, these effects protect the ocular surface from dryness and absorb shear forces of the blink, and assist the eye's own secreted gel forming mucins (predominantly MUC5) in maintaining their viscoelastic properties and ensuing structure and stability of the tear film, thereby slowing or preventing the changes to the ocular surface seen in dry eye conditions.

Although mucins can be obtained from various sources, they have similar structures for the particular molecules described above (MUC 1, 2, etc.) among species, particularly with regard to the protein backbone. They are glycoproteins containing from fifty to eighty percent carbohydrate. They are large, elongated molecules (molecular weight $10^5$ to $10^7$ daltons) with a protein backbone to which oligosaccharides are attached in a bottle-brush configuration. The oligosaccharide side chains, or bristles, can be highly variable in their make-up, indicating that the more basic functions of the molecule derive from the protein core. These molecules can be crosslinked through disulfide bridges to form very high molecular weight gels. MUC1 and MUC4, the surface or transmembrane mucin molecules, are the smallest mucins and are not considered gel forming mucins on their own, although cleaved parts of the molecules can be found in soluble form.

The mucins used in exemplary ophthalmic compositions are of the MUC1 and MUC4 type, and are derived from the surface of glandular and ductal epithelial cells. Such mucin can be collected by extracting it from the tissue, either by subjecting the surface or its associated secretion, such as bile or saliva, to liquid extraction or by mechanical (scraping) means. From the research on its role in tumor cell proliferation, more is known about MUC1. Mucin of the MUC1 type can also be derived from tumor cell lines, such as colon carcinoma. MUC1 can also be isolated from mammalian milk, particularly bovine, or milk byproducts, such as whey.

Recovery and purification of MUC1 from its source can be carried out utilizing standard methods known in the art. Published studies on the structure and function of mucin have led to several preferred isolation techniques. These would include, but are not limited to, cell disruption, membrane filtration and microfiltration, tangential flow filtration, chromatography (e.g., size exclusion, ion exchange, affinity), extraction, adsorption, precipitation (with nonsolvent, salts, etc.) density gradient fractionation, electrophoresis, electrodialysis and isoelectric focusing. The MUC1 that results can be in the form of a hydrocolloid, which is a complex of the MUC1 linked to lower molecular weight proteins through disulfide bridges. This complex molecular structure contains from about fifty percent to seventy percent or higher MUC1, and may contain a lipid component as well.

The scientific literature reveals a number of techniques for characterizing the various types of mucins, and in particular MUC1. These techniques include, but are not limited to, chromatographic techniques or gel electrophoresis, particularly SDS-PAGE, followed by direct protein staining, (e.g., silver staining) or immunohistochemical staining (e.g., Western blotting or Northern blotting), and immunoprecipitation techniques, amino acid analysis, hexosamine and hexuronic acid determination, carbohydrate determination, lectin binding probes, such as jaclin, light scattering, scanning electron microscopy, mass spectrometry, mucin nitrogen content and ash.

The amount of mucin in an ophthalmic formulation can vary greatly depending on the product type. For example, in contact lens related solutions the mucin concentration would vary from about 0.001% to 5.0% by weight. In dry eye preparations the mucin level could vary from about 0.1% to about 10.0% by weight. In a solid ocular insert delivery device the mucin level could range to about 90.0% or greater by weight. Within each type of preparation, the concentration might be varied, depending on such factors as the severity of the dry eye condition being treated, to enhance particular properties of the mucin solution. These ranges are for purpose of illustration and are not meant in any manner to limit the scope of the claims.

Exemplary ophthalmic compositions include a transmembrane or surface mucin (e.g., MUC1 or MUC4) from any number of the exemplary sources described hereinbefore. In addition, other solution components may be employed as required:

Viscosifiers

Cellulose derivatives are commonly used to increase viscosity. Specific cellulose derivatives include: hydroxypropylmethylcellulose, carboxymethylcellulose, methylcellulose, hydroxyethylcellulose, etc. Some polysaccharides may also be utilized to increase the viscosity of ophthalmic solutions and include xanthan, scleroglucan, carrageenans, tragacanth gum, hyaluronic acid etc. Other viscosifiers that are useful include polyvinylpyrrolidone, polyvinyl alcohol, polyethyleneoxide, polyacrylic acid and crosslinked polyacrylic acid. Generally, viscosifiers are present in the amount of 0.1 to 0.75% by weight of the solution.

Buffering Agents

Any pharmaceutically acceptable buffer system may be utilized and include phosphates, borates, citrates, acetates and carbonates in amounts necessary to produce a pH of about 6.0 to about 8.0.

Tonicity Agents

The tonicity of the ophthalmic solutions described here can be adjusted to either hypotonic, isotonic or hypertonic relative to normal tears by use of generally used materials know to the art. Sodium and potassium chloride are widely used to adjust tonicity. Other agents include dextrose, mannitol, sorbitol and urea.

Humectants

Water binding compounds aid in retaining moisture on the ocular surface and include glycerin, propylene glycol, polyethylene glycol.

Wetting Agents

Certain compounds are useful to promote surface wetting, whether it be the ocular surface or the surface of a contact lens. One category that is preferred is the polyoxamers. These polyethyleneoxide-polypropyleneoxide-polyethyleneoxide block copolymer are available from BASF. Other compounds include the Tetronics®, reverse Pluronics® and the reverse Tetronics®, also available from BASF.

Preservatives

The exemplary compositions may include a preservative in an effective amount. Preservatives known to the art include alkyldimethyl benzylammonium chloride (BAK), chlorhexidene gluconate (CHG), polyhexamethylene biguanide (PHMB), other polyquats and sorbic acid. The exemplary compositions may also include a co-preservative and/or chelating agent, such as ethylenediaminetetraacetic acid (EDTA) and its salts.

Other Additives

In some cases it may be beneficial to include other components in an ophthalmic solution. These include specific ions, such as Ca++, Zn++ and Mg++, Cu++, selenium, vitamins, such A, C and E, to promote ocular health. The exemplary ophthalmic compositions described herein may also be utilized as vehicles for drug delivery. Drugs often used in the eye include anti-glaucoma compounds, anti-inflammatory agents and anti-infective agents.

Examples of ophthalmic drugs include antibiotics such as tetracycline, chlortetracycline, bacitracin, neomycin, polymyxin, gramicidin, cephalexin, oxytetracycline, chloramphenicol, kanamycin, rifampicin, tobramycin, gentamicin, erythromycin and penicillin; antibacterials such as sulfonomides, sulfadiazine, sulfacetamide, sulfamethizole and sulfisoxazole, nitrofurazone and sodium propionate; antivirals including idoxuridine, trifluorothymidine, acyclovir, gancyclovir and interferon; non-antibiotic, anti-infection, anti-bacterial or anti-microbial drugs such as iodine based preparation triclosan, chlorhexidine, et al; anti-allergenics such as sodium cromoglycate, antazoline, methapyrine, chlorpheniramine, cetirizine and prophenypyridadine; anti-inflammatories such as hydrocortisone, hydrocortisoneacetate, dexamethasone, dexamethasone 21-phosphate, fluorocinolone, medrysone, prednisolone acetate, luoromethalone, hypothalamus releasing factor; beta adrenergic blockers such as timolol maleate, levobunclol HCl and betaxolol HCl; growth factors such as epidermal growth factor and fibronectin; carbonic anhydrase inhibitors such as dichlorphenamide, betamethasone, and triamcinolone and non-steroidal agents such as indomethacin, diclofenac, flurbiprofen, piroxicam, ibuprofen and acetylsalicylic acid; decongestants such as phenylephrine, naphazoline and tetrahydrozoline: miotics and anticholinesteras such as pilocarpine, acetylcholinechloride, physostigmine, eserine, carbachol, di-isopropylfluorophosphate, phospholineiodine, and demecarium bromide; mydriatics such as a tropine sulfate, cyclopentolate, homatropine, scopolamine, tropicamide, eucatropine, and hydroxyamphetamine; sympathomimetics such as epinephrine; immunological drugs such as vaccines and immunostimulants; hormonal agents such as estrogens, estradiol, progestational, progesterone, insulin, calcitonin, parathyroidhormone and peptide, vasopressin, acetazolamide and methazolamide and other drugs such as prostaglandins antiprostaglandins, and prostaglandin precursors; angiogenesis inhibitors such as liferative agents such as flurouracil and mitomycin.

As previously described, the exemplary ophthalmic compositions finds particular utility as lubricating eye drops, i.e., an artificial tear solution, a tear fluid supplement, a delivery vehicle for topical ophthalmic drug application. In most of these applications, the compositions are provided in a buffered, sterile aqueous solution. Typically, these solutions have a viscosity from about 1 to 100 cps. As a solution the compositions are dispensed in the eye in the form of an eye drop. It should be understood, however, that the compositions described herein may also be formulated as viscous liquids, i.e., viscosities from several hundred to several thousand cps, gels or ointments. In these applications the mucin component would be dispersed or dissolved in an appropriate vehicle such as Lubragel, GRR Lubricating Jelly or Karajel, all trademarked products of United-Guardian, Inc., Hauppauge, N.Y.

The exemplary compositions may also be formulated as solid ocular inserts that dissolve or erode over time when placed in the cul-de-sac of the eye.

Swelling-controlled release devices would consist of mucin homogeneously dispersed in a glassy polymer such as a water soluble cellulosic. When the insert is placed in the eye, the tear fluid begins to penetrate the matrix, followed by swelling, and finally dissolution, of the matrix. As this process occurs, mucin is released into the eye to provide relief of dry eye symptoms over a long period of time.

Erodible devices would again consist of mucin homogeneously dispersed in a polymer matrix. In this case, mucin is released by a chemical reaction (hydrolysis) that results in solubilization of the matrix polymer, usually at the surface of the device. Generally, the matrix material is a polyanhydride or a poly(ortho ester).

In another embodiment the mucin may be chemically modified or crosslinked to act as its own "matrix", where mucin comprises the entire, or nearly entire, device, thus providing the maximum amount of mucin available to the eye.

Furthermore, in some contact lens related embodiments, the exemplary transmembrane or surface mucin disclosed herein may be incorporated into contact lens soaking and conditioning solutions as well as lubricating eye drops for contact lens wearers.

In another embodiment the mucin may be utilized in drug delivery. The most common and convenient method for delivery of ocular drugs is by way of topical eye drops. Generally, the solution vehicles employed are quickly diluted by the tear fluid and drain from the eye in a matter of minutes. This short residence time hinders the absorption and hence the bioavailability of the drug in the eye. Oftentimes the short residence time is overcome by greatly increasing the concentration of the drug to improve bioavailability. This often leads to significant undesirable side effects due to the systemic actions of many of the ocular drugs currently prescribed.

Much research has been done to improve the residence time of the drug vehicle at the ocular surface and also to promote interaction or association of the drug with the vehicle. One approach that has been commercialized is to utilize a crosslinked carboxy-functional polymer such as Carbopol®, supplied by B.F. Goodrich. The bioadhesive nature of this polymer has been the basis for controlled release ophthalmic formulations as described in U.S. Pat. No. 4,615,697 and U.S. Pat. No. 5,188,826, both of which are incorporated by reference in their entirety.

These crosslinked carboxy-functional polymers swell in aqueous solution but remain as micron-size hydrated particles. Furthermore, at neutral pH, they are substantially anionic in nature. Since many ophthalmic drugs, for example timolol and pilocarpine, are positively charged, they will associate with the negatively charged polymer particles through electrostatic interaction. Also, since the hydrated particles are microporous, the drug can be absorbed into the matrix. When an ophthalmic solution of this type is placed in the eye, the hydrated polymer particles adhere to the mucosal surface, providing extended residency time. During this residence the drug is released from the hydrated polymer particles, thus providing for a more efficient local delivery to the eye.

The transmembrane or surface mucins, MUC1 and MUC4, used in the exemplary compositions are by definition "bioadhesive" and contain multiple negative charges. It has also been shown that the mucins of this invention can exist as hydrocolloid particles. Given this information one would expect the mucins of this invention to act in a similar manner to the crosslinked carboxy-functional polymers as an ophthalmic drug delivery vehicle. In practice, these transmembrane or surface mucins provide superior retention time due to their ability to interact not only with the epithelial surface but also with the natural mucins in the tear film.

As an illustration of the exemplary mucin-containing compositions, several examples are provided below. A key to the ingredients used in the Examples is given in Table I.

TABLE I

| INGREDIENT | TRADE NAME | % ACTIVE | SUPPLIER |
| --- | --- | --- | --- |
| Hydroxethyl cellulose | Natrosol 250 MR | 100 | Hercules |
| Hydroxypropylmethyl cellulose | Methocel E4M | 100 | Dow |
| Polysorbate | Tween 80 | 100 | ICI Americas |
| Block copolymer of ethyleneoxide/propylene oxide | Pluronic F127 | 100 | BASF |
| Polyvinyl alcohol 80 | | 100 | Polysciences |
| Chlorhexidine gluconate | CHG | 20 | Xttrium Labs |
| Polyhexamethyl biguanide HCl | PHMB | 20 | ICI Americas |
| Polyglycerol methacrylate | Lubrigel | Varies | United-Guardian |
| Timolol maleate | | 100 | Sigma |
| Pilocarpine HCl | | 100 | Sigma |
| Polyvinyl alcohol | Airvol 325 | 100 | Air Products |

EXAMPLE 1

There are many source of transmembrane or surface mucin (i.e., MUC1 mucin) and a variety of procedures for recovering that mucin. Given this scope, the following example describes a detailed procedure for isolating MUC1 mucin from acid whey, a byproduct of cheese production. It will be understood that this source is merely an exemplary source and the isolation techniques are also merely exemplary as other techniques are available. While, MUC1 is being described as an exemplary transmembrane or surface mucin, it will be appreciated that MUC4 is also classified as a transmembrane or surface mucin. Because of the greater availability of MUC1, it is the subject of the following examples.

Unconcentrated acid whey, after a heat sterilization step, is filtered through a 0.65 $\mu$m membrane to remove large particles. The permeate is then concentrated and washed with 1 M NaCl on a membrane with a 1,000,000 MW cut-off to remove low MW proteins and lactose. The concentrated solution is then autoclaved, which denatures the remaining proteins except mucin. The denatured proteins are removed by refiltering the solution on a 0.22 $\mu$m membrane. The mucin is then concentrated and desalted by washing with water on the 1,000,000 MW filter. The final yield is around 0.25 gm of MUC1 mucin per liter of unconcentrated acid whey (0.25 g/l).

EXAMPLE 2

The MUC1 mucin recovered from acid whey, in Example 1, was analyzed by polyacrylamide gel electrophoresis (SDS-PAGE) and found to contain three mucin bands along with trace amounts of other proteins. The structure of the mucin fractions was then determined with respect to total protein, lipid and carbohydrate content. The surface activity and the size of the mucin hydrocolloid were also determined. The results of the characterization are reported in Table II.

TABLE II

| Composition (%) | | | Surface tension | Size |
| --- | --- | --- | --- | --- |
| Protein | Carbohydrate | Lipid | (mN/m) | ($\mu$m) |
| 28.80 | 33.89 | 30.82 | 52.00 | 283.18 |

EXAMPLE 3

This example illustrates the ability of MUC1 mucin solutions to be sterilized by autoclaving.

A 20 ml solution of 0.5% by weight mucin (derived from acid whey) in water was prepared. The solution was then filtered through a 5.0 $\mu$m filter, under clean conditins, and divided among four 10 ml vials (5 ml in each). The vials were then sealed with a crimp/septum assembly. Two of the sealed vials were autoclaved at 121° C. for 50 minutes. The other two were unprocessed controls. Stability tests were performed at both room temperature and 35° C., on both the autoclaved and unprocessed control samples. The samples were observed on a weekly basis over four weeks for any visual changes or differences. The results are summarized below in Table III.

TABLE III

| Condition | Initial | 1 Week | 2 Weeks | 3 Weeks | 4 Weeks |
| --- | --- | --- | --- | --- | --- |
| Unprocessed, RT | C | C | C | C | C |
| Autoclaved, RT | C | C | C | C | C |
| Unprocessed, 35° C. | C | C | C | C | C |
| Autoclaved, 35° C. | C | C | C | C | C |

Compatibility Key: C-Compatible, homogeneous; SI-Slightly incompatible, some precipitation; I-Incompatible, gross precipitation No visual changes in color, clarity or appearance were noted as a result of autoclaving. The results indicate that the MUC1 mucin can be autoclaved with no apparent degradation. This finding indicates that milk mucin-based ophthalmic solutions can be sterilized by an autoclave process.

EXAMPLE 4

This example illustrates the compatibility of MUC1 mucin with common (monograph) ophthalmic solution ingredients. To accomplish this task, acid whey-derived mucin-based solutions were prepared by dissolving, with stirring, the ingredients in the required amount of USP/NF purified water (qs to 100%). A total of 20 ml of each solution was prepared.

The non viscous solutions were filtered through a 5.0 micron syringe filter, divided into three equal volumes, each being placed in a 10 ml vial, which was then sealed with a crimp/septum assembly. The vials were autoclaved at 121° C. for 50 minutes to sterilize the solutions. The solution samples were then aged, at three temperatures, 10° C., RT and 35° C., for 28 days. The samples were visually inspected for signs of incompatibility (precipitation) and stability (color change) at 3, 7, 14, and 28 days. The inspection results were recorded and are presented in Table IV, using the same key for compatibility as Table III.

It can be seen from the data in Table IV that incompatibility was noted with only one solution component, polyethylene glycol. The other solutions components were compatible with milk mucin and produced solutions that were stable over the 28-day shelf life test.

EXAMPLE 5

This example illustrates the ocular compatibility of MUC1 mucin utilizing an in vitro transepithelial permeability assay.

The irritation potential of MUC1 mucin was evaluated at a level of 3.0% in two buffers. These two buffers are representative of those utilized in a commercial ophthalmic solution products. Formulations details are presented in Table V.

TABLE V

| Component | A | B |
| --- | --- | --- |
| Mucin (derived form acid whey) | 3.00 | 3.00 |
| Sodium pbosphate, dibasic | 0.28 | — |
| Potassium phosphate, monobasic | 0.055 | — |
| Boric acid | — | 0.35 |
| Sodium borate | — | 0.05 |
| Sodium chloride | 0.42 | 0.47 |
| Disodium edetate | 0.05 | 0.05 |
| Propylene glycol | 0.50 | 0.50 |
| Deionized water, qs to | 100 | 100 |

The solutions described in Table V were subjected to the following experiments to determine potential eye irritation of the solutions. The experimental methods follow the procedure developed by R. Tchao, which is described in "Trans-Epithelial Permeability of Fluorescein In Vitro as an Assay to Determine Eye Irritants", Progress in In Vitro Toxicology, Volume 6, 1988, pages 271–283 (Mary Ann Liebert, Inc. Publishers, New York), the disclosure of which is incorporated herein by reference. The Tchao technique is described as a method of determining potential eye irritation of a substance by correlating damage to a mono-layer of Madin-Darby Canine Kidney (MDCK) cells with damage to corneal epithelial cells. The amount of fluorescein passing through the cell mono-layer is a function of permeability of the cell mono-layer. Higher cell mono-layer permeability indicates greater damage to the cell junctions from application of a test solution thereto, whereas lower cell mono-layer permeability indicates less severe damage to the cell junctions from application of the test solution.

The details of the test are presented below.

Culture preparation: MDCK cells are obtained from ATCC, and maintained in minimum essential medium (MEM) supplemented with 10% bovine calf serum with iron supplementation (Hyclone, Utah). Stock cultures are passaged weekly using trypsin and EDTA. Cultures are used before passage 50. For the test, 0.5 ml of a cell suspension containing 2×10 E5 cells are seeded in Millicell HA 13 mm inserts (Millipore, Bedford, Mass.). The inserts are placed in 24-well plates and fed with 0.5 ml medium. Two days after seeding the cells, the media both inside and outside the inserts are replaced with fresh media. On day 6 after seeding, the inserts are used for testing the solutions. It has been shown that the resistance developed by a confluent MDCK monolayer is about 600 ohms/cm$^2$.

Test: Each insert is rinsed with Hanks Balanced Salt Solution (HBSS) 3×1 ml using a 10 ml syringe without needle. Each test solution (0.5 ml) is added to the inside of an insert that has been placed in a fresh 24-well plate. Triplicate inserts are used for each test solution. The 24-well plate with inserts and test solutions are placed in a humidified incubator at 37° C. for 30 minutes. Each series of triplicates is handled sequentially to allow exact timing of the treatment. After incubation, sequentially, each insert is individually rinsed with HBSS 5×1 ml using the 10 ml syringe, and is placed in a fresh 24-well plate containing 0.5 ml HBSS in each well. 0.5 ml of a solution of Na-fluorescein (3 mg/100 ml) is added to each rinsed insert. After incubation at room temperature for 30 minutes, the inserts are sequentially removed from the wells, and the amount of Na-fluorescein in each of the wells is measured in a CytoFluor 2300, using 540 nm excitation and 590 nm emission. For each test, the negative control is HBSS and the positive control is 250 µg/ml sodium dodecyl sulfate (SDS). It has been determined that the assay can measure the effect of 50 µg/ml SDS, and the effect on the permeability of the monolayer is linearly proportional to the concentrations of SDS from 50–250 µg/ml. Fluorescence units (arbitrary) of each test solution is plotted against test solutions.

Interpretation of results: The results are expressed as % of SDS response, and comparisons with the HBSS response. Generally, if the solution is 20% of the SDS response, the solution may be a mild irritant.

The results of the in vitro irritation potential testing are presented in Table V along with the results for the positive and negative controls. The positive control 250 ppm of sodium dodecyl sulfate (SDS) is known to cause noticeable irritation when instilled in the human eye. The negative control Hank's balanced salt solution (HBSS) is known not to elicit any adverse reaction when instilled in the human eye. The results are expressed as a percentage of SDS response, that is, SDS=100% response. Any response less than 20% indicates little or no tissue change and is considered non-irritating.

TABLE VI

| Solution | Response |
| --- | --- |
| SDS (250 ppm) | 100 |
| A | 6.5 ± 0.1 |
| B | 5.4 ± 0.2 |
| HBSS | 3.9 ± 0.7 |

It can be seen that the response of mucin, even at a level of 3%, is similar to the negative control, and therefore should be completely compatible with the ocular environment.

EXAMPLE 6

The following example illustrates the use of MUC1 mucin in two dry eye formulations. The formulations were subjected to one week of aging at three temperature levels. The formulations and physical properties are presented in Table VII.

TABLE VII

| Component | A | B |
|---|---|---|
| Mucin | 0.5 | 0.5 |
| Sodium phosphate, dibasic | 0.28 | — |
| Potassium phosphate, monobasic | 0.055 | — |
| Boric acid | — | 0.35 |
| Sodium borate | — | 0.05 |
| Sodium chloride | 0.42 | 0.42 |
| Disodium edetate | 0.05 | 0.05 |
| Potassium sorbate | 0.15 | 0.15 |
| Propylene glycol | 0.50 | 0.50 |
| HEC Natrosol 250 MP | 0.30 | 0.40 |
| Pluronic ® F127 | 1.0 | 1.0 |
| Polysorbate 80 | 0.5 | 0.5 |
| Deionized water, qs to | 100 | 100 |
| Physical Properties, Initial | | |
| pH | 7.3 | 7.0 |
| Osmolality | 292 | 300 |
| Viscosity | 12 | 29 |
| Surface Tension | 39 | 39 |
| Physical Properties, 7 days at 10° C. | | |
| pH | 7.3 | 7.0 |

TABLE VII-continued

| Component | A | B |
|---|---|---|
| Osmolality | 290 | 300 |
| Viscosity | 12 | 30 |
| Surface Tension | 39 | 39 |
| Physical Properties, 7 days at RT | | |
| pH | 7.3 | 7.0 |
| Osmolality | 292 | 300 |
| Viscosity | 13 | 30 |
| Surface Tension | 39 | 39 |
| Physical Properties, 7 days at 35° C. | | |
| pH | 7.3 | 7.0 |
| Osmolality | 293 | 301 |
| Viscosity | 12 | 29 |
| Surface Tension | 39 | 39 |

From the results it can be seen that the physical properties of both Solution A and B are stable over the one-week aging period at all three temperature levels.

EXAMPLE 7

The treatment of dry eye and other ocular discomfort often involves the use of an ointment or gel. The ointment or gel can be either water soluble or non-water soluble (petrolatum based). This example employs a water soluble gel polymer, poolyglycerol methacrylate, as the vehicle for delivering MUC1 mucin to the ocular environment. Gels of this type can be obtained from United-Guardian, Inc.; Hauppauge, N.Y., under the brand name Lubragel®. The following formulations (in weight percent) were prepared by incorporating all the ingredients, except the Lubragel®, into the aqueous phase. The Lubragel® was then mixed with the aqueous phase to produce the final product. The following formulations are representative of MUC1 mucin-based gels, ointments and viscous liquids products for ophthalmic use (Table VIII).

TABLE VIII

| INGREDIENT | A | B | C | D | E | F |
|---|---|---|---|---|---|---|
| Lubragel ® DV | 35.0 | — | — | 23.50 | — | — |
| Lubragel ® CG | — | 45.0 | — | — | 30.00 | — |
| Lubragel ® MS | — | — | 55.0 | — | — | 37.00 |
| Milk Mucin | 1.0 | 1.0 | 1.0 | 0.67 | 0.67 | 0.67 |
| Glycerin | 3.0 | 3.0 | 3.0 | 1.00 | 1.00 | 1.00 |
| Propylene Glycol | 1.0 | 1.0 | 1.0 | 0.67 | 0.67 | 0.67 |
| Sodium Bicarbonate | 0.1 | 0.1 | 0.1 | 0.07 | 0.07 | 0.07 |
| Chlorhexidine Gluconate (20%) | 0.004 | 0.004 | 0.004 | 0.003 | 0.003 | 0.003 |
| Deionized water, qs to | 100% | 100% | 100% | 100% | 100% | 100% |
| Viscosity, cps | 42,000 | 27,000 | >100,000 | 18,400 | 13,300 | 90,500 |
| Appearance | Gel | Gel | Stiff gel | Thick liquid | Thick liquid | Gel |

The above results demonstrate the ability of MUC1 mucin to be incorporated into ophthalmic delivery vehicles of widely different viscosities.

EXAMPLE 8

The following formulations (in weight %) illustrate the use of mucin as an interactive component with cationic drugs in glaucoma eye drop solutions (Table IX).

TABLE IX

| INGREDIENT | A % | B % |
| --- | --- | --- |
| Timolol maleate | 0.25 | — |
| Pilocarpine | — | 1.0 |
| Milk mucin | 0.75 | 0.75 |
| Boric acid | 0.35 | 0.35 |
| Sodium borate | 0.05 | 0.05 |
| Sodium chloride | 0.42 | 0.42 |
| Propylene glycol | 0.50 | 0.50 |
| Polysorbate 80 | 0.50 | 0.50 |
| Disodium edetate | 0.05 | 0.05 |
| Potassium sorbate | 0.20 | 0.20 |
| Deionized water, qs to | 100 | 100 |

The formulations presented are prepared by dissolving all the ingredients in deionized water. After the ingredients have completely dissolved, the formulation is stirred for at least two hours before properties are measured.

|  | A | B |
| --- | --- | --- |
| pH | 7.20 | 6.07 |
| Osmolality mosm/kg | 326 | 401 |
| Viscosity, cps | 1.5 | 1.4 |
| Appearance | Hazy | Hazy |

The above results demonstrate the use of MUC1 mucin as a delivery vehicle for ophthalmic drugs.

EXAMPLE 9

The following formulations (in weight %) illustrate the use of milk mucin in soft contact lens rinsing, soaking and disinfecting solutions (Table X).

TABLE X

| INGREDIENT | A % | B % | C % | D % |
| --- | --- | --- | --- | --- |
| Milk mucin | 0.50 | 1.0 | 0.50 | 1.0 |
| Pluronic F127 | — | — | 1.0 | 2.0 |
| Tetronic 1107 | 1.0 | 2.0 | — | — |
| Propylene glycol | — | 0.50 | 0.50 | — |
| Sodium chloride | 0.70 | 0.40 | 0.15 | 0.40 |
| Disodium phosphate | 0.28 | 0.28 | — | — |
| Potassium phosphate | 0.06 | 0.06 | — | — |
| Boric acid | — | — | 0.65 | 0.65 |
| Sodium borate | — | — | 0.12 | 0.12 |
| Disodiumedetate | 0.10 | 0.10 | 0.10 | 0.10 |
| PHMB (actual) | 15 ppm | 15 ppm | — | — |
| Potassium sorbate | — | — | 0.25 | 0.25 |
| Deionized water, qs to | 100 | 100 | 100 | 100 |

The formulations presented are prepared by dissolving all the ingredients in deionized water. After the ingredients have completely dissolved, the formulation is stirred for at least two hours before properties are measured.

|  | A | B | C | D |
| --- | --- | --- | --- | --- |
| pH | 7.13 | 7.20 | 7.40 | 7.30 |
| Osmolality mosm/kg | 313 | 292 | 308 | 320 |
| Viscosity, cps | 2.0 | 2.3 | 2.1 | 2.6 |
| Appearance | Hazy | Hazy | Hazy | Hazy |

The above results demonstrate the utility of MUC1 mucin as an active component in a soft contact lens solution.

EXAMPLE 10

The following formulations (in weight %) illustrate the use of milk mucin for contact lens in-eye rewetting and lubricating solutions (Table XI).

TABLE XI

| INGREDIENT | A % | B % | C % | D % |
| --- | --- | --- | --- | --- |
| Milk mucin | 1.0 | 2.0 | 1.0 | 2.0 |
| Methocel E4M | 0.30 | 0.20 | 0.30 | 0.20 |
| Pluronic F127 | — | — | 0.50 | 0.50 |
| Tetronic 1107 | 0.50 | 0.50 | — | — |
| Propylene glycol | — | — | 0.30 | 0.50 |
| Polyvinyl alcohol 80 | 0.30 | 0.10 | — | — |
| Sodium chloride | 0.60 | 0.60 | 0.20 | 0.10 |
| Disodium phosphate | 0.28 | 0.28 | — | — |
| Potassium phosphate | 0.06 | 0.06 | — | — |
| Boric acid | — | — | 0.75 | 0.75 |
| Sodium borate | — | — | 0.15 | 0.15 |
| Disodium edetate | 0.07 | 0.07 | 0.07 | 0.07 |
| PHMB (actual) | 15 ppm | 15 ppm | — | — |
| Potassium sorbate | — | — | 0.25 | 0.25 |
| Deionized water, qs to | 100 | 100 | 100 | 100 |

The formulations presented are prepared by dissolving all the ingredients in deionized water. After the ingredients have completely dissolved, the formulation is stirred for at least two hours before properties are measured.

|  | A | B | C | D |
| --- | --- | --- | --- | --- |
| pH | 7.20 | 7.10 | 7.40 | 7.40 |
| Osmolality mosm/kg | 278 | 287 | 333 | 304 |
| Viscosity, cps | 12.1 | 7.6 | 13.3 | 7.7 |
| Appearance | Hazy | Hazy | Hazy | Hazy |

The above results demonstrate the utility of MUC1 mucin as an active ingredient in a contact lens rewetting/lubricating solution.

EXAMPLE 11

The transmembrane or surface mucin (MUC1) derived form a mammalian source finds particular utility as packaging solutions for soft hydrogel contact lenses. The following composition illustrates the use of mucin in a contact lens packaging solution (Table XII).

TABLE XII

| INGRBDIENT | A % | B % | C % | D % |
| --- | --- | --- | --- | --- |
| Milk mucin | 1.0 | 2.0 | 1.0 | 2.0 |
| Boric acid | 0.35 | 0.35 | — | — |
| Sodium borate | 0.05 | 0.05 | — | — |
| Disodium phosphate | — | — | 0.28 | 0.28 |
| Potassium phosphate | — | — | 0.055 | 0.055 |
| Sodium chloride | 0.69 | 0.69 | 0.72 | 0.72 |
| Deionized water, qs to | 100 | 100 | 100 | 100 |

The formulations presented are prepared by dissolving all the ingredients in deionized water. After the ingredients have completely dissolved, the formulation is stirred for at least two hours before properties are measured.

|  | A | B | C | D |
|---|---|---|---|---|
| pH | 7.5 | 7.4 | 7.3 | 7.3 |
| Osmolality mosm/kg | 293 | 305 | 302 | 303 |

The above results demonstrate the ability of MUC1 mucin to function as an active ingredient in a contact lens packaging solution.

EXAMPLE 12

The following formulations (in weight %) illustrate the use of milk mucin as a dry eye treatment solution (Table XIII).

TABLE XIII

| INGREDIENT | A % | B % |
|---|---|---|
| Milk mucin | 0.5 | 1.0 |
| Disodium phosphate | 0.28 | 0.28 |
| Potassium phosphate | 0.055 | 0.055 |
| Sodium chloride | 0.72 | 0.72 |
| Disodium edetate | 0.05 | 0.05 |
| Deionized water, qs to | 100 | 100 |

The formulations presented are prepared by dissolving all the ingredients in deionized water. After the ingredients have completely dissolved, the formulation is stirred for at least two hours before properties are measured.

| pH | 7.2 | 7.2 |
|---|---|---|
| Osmolality mosm/kg | 300 | 300 |
| Appearance | Slight haze | Hazy |

The above solutions were filtered through a 0.22 micron filter, in a clean room, into eye drop bottles. The solutions were then placed in the eyes of two subjects in a controlled clinical setting. The eyes of the subjects were monitored through a slit lamp biomicroscope after instillation of a drop of the test solutions. A Keeler Tearscope was also utilized to observe the effects on the subject tear film.

SUMMARY OF PROCEDURE

Solutions A and B (concentrations of 0.5% w/w and 1.0% w/w) were tried on subject one without RGP contact lens in place, and then lenses were placed in eye after soaking in A for a few minutes. Trials were bilateral for subject one. In subject two, A was instilled in one eye, and Visine Tears was instilled in the contralateral eye.

Adding one drop to the eye both with and without contact lenses in place produced no adverse reactions, including no symptoms of irritation, foreign body sensation, burning, dryness, decreased vision, and no signs of corneal edema, conjunctival redness, conjunctival edema, or discharge. There was no punctate staining observed with addition of fluorescein stain. Additionally, there was no erythema or edema of the adnexa by external examination.

Examination of the tear film using the Keeler Tearscope revealed a slightly more stable appearing tear film, as indicated by interblink film appearance and motion and a more predominantly blue lipid pattern of more uniform wave appearance. This was true for all eyes receiving either mucin drop, but was not seen with the Visine Tears instilled into subject two OS.

Although the number of eyes looked at was limited, the important initial finding is that the mucin drops did not cause any adverse reactions as listed above or even discomfort. The findings describing a more stable and/or thicker tear film are advantageous.

As used herein, the term "mucin-containing component" refers to a molecular complex containing mucin as one of the components complexed with one or more other molecular components, such proteins (e.g., glycoproteins) and lipids. The mucin-containing component may contain minor amounts of lactose and salts under some circumstances; however, these components are preferably removed during an isolation and purification process.

It will be understood that the ophthalmic preparation may contain only a purified transmembrane mucin. In other embodiments, the transmembrane mucin is part of the mucin-containing component and is present in an amount from about 50% to about less than 100% by weight of the mucin-containing component. In other embodiments, the transmembrane mucin is present in an amount from about 60% to about 90% by weight of the mucin-containing component.

While preferred embodiments have been shown and described, various modifications and substitutions may be made thereto without departing from the spirit and scope of the present invention. Accordingly, it is to be understood that the present invention has been described by way of illustrations and not limitation.

What is claimed is:

1. An ophthalmic preparation including:
a transmembrane mucin.

2. An ophthalmic preparation in accordance with claim 1, wherein the transmembrane mucin is classified as one of a MUC1 mucin and MUC4 mucin.

3. An ophthalmic preparation in accordance with claim 1, wherein the preparation is in a form selected from the group consisting of a solution, an ointment, a gel, and an ocular insert.

4. An ophthalmic preparation in accordance with claim 1, wherein the transmembrane mucin is derived from mammalian milk or a milk byproduct.

5. An ophthalmic preparation in accordance with claim 4, wherein the transmembrane mucin is classified as MUC1 mucin.

6. An ophthalmic preparation in accordance with claim 1, further comprising at least one component selected from the group consisting of a buffering agent, a viscosity modifying agent, a tonicity modifying agent, a humectant compound, and a therapeutic drug.

7. An ophthalmic preparation in accordance with claim 4, wherein said milk byproduct comprises whey which is purified to recover the transmembrane mucin.

8. An ophthalmic preparation in accordance with claim 1, wherein the transmembrane mucin is autoclavable.

9. An ophthalmic preparation in accordance with claim 1, wherein the transmembrane mucin is derived from a surface of one of glandular and ductal epithelial cells.

10. An ophthalmic preparation in accordance with claim 1, wherein the transmembrane mucin is a part of a mucin-containing component.

11. An ophthalmic preparation in accordance with claim 10, wherein the mucin-containing component includes glycoproteins.

12. An ophthalmic preparation in accordance with claim 10, wherein the transmembrane mucin is greater than 50% by weight of the mucin-containing component.

13. An ophthalmic preparation in accordance with claim 1, wherein the transmembrane mucin is disposed in an acqueous solution for treating a contact lens to provide a protective coating surfaces of the contact lens.

14. An ophthalmic preparation in accordance with claim 10, wherein the transmembrane mucin is present in an amount from about 50% to less than 100% by weight of the mucin-containing component.

15. An ophthalmic preparation for treating an eye by topically applying the preparation to an ocular surface to provide lubrication and protection to the ocular surface for the relief of dryness and discomfort symptoms, the ophthalmic preparation including:

a buffered, sterile aqueous solution including a transmembrane mucin.

16. An ophthalmic preparation in accordance with claim 15, wherein the transmembrane mucin is classified as one of a MUC1 mucin and MUC4 mucin.

17. An ophthalmic preparation in accordance with claim 15, wherein the transmembrane mucin is classified as MUC1 mucin.

18. An ophthalmic preparation in accordance with claim 15, wherein the transmembrane mucin is derived from mammalian milk or a milk byproduct.

19. An ophthalmic preparation in accordance with claim 18, wherein said milk byproduct comprises whey which is purified to recover the transmembrane mucin.

20. An ophthalmic preparation in accordance with claim 15, wherein the transmembrane mucin is derived from a surface of one of glandular and ductal epithelial cells.

21. An ophthalmic preparation in accordance with claim 15, wherein the transmembrane mucin is formed entirely of mucin having a single mucin classification.

22. A method for treating an eye to provide lubrication and protection to an ocular surface of the eye for the relief of dryness and discomfort symptoms, the method comprising:

topically applying an ophthalmic preparation to the ocular surface, the ophthalmic preparation including a transmembrane mucin.

23. A method in accordance with claim 22, wherein the transmembrane mucin is classified as one of a MUC1 mucin and MUC4 mucin.

24. A method in accordance with claim 22, wherein the transmembrane mucin is classified as MUC1 mucin.

25. A method in accordance with claim 22, further comprising:

deriving the transmembrane mucin from mammalian milk or a milk byproduct in the form of MUC1 mucin.

26. A method in accordance with claim 25, wherein deriving the transmembrane mucin includes:

processing the mammalian milk or milk byproduct to remove at least one of sugars, carbohydrates, salts, proteins, and lipids to recover a purified transmembrane mucin.

27. A method in accordance with claim 22, further comprising:

deriving the transmembrane mucin from a surface of one of glandular and ductal epithelial cells.

28. A method of treating an eye for dryness and other discomfort symptoms, the method comprising:

preparing a buffered, sterile aqueous solution including a transmembrane mucin; and topically applying the solution to an ocular surface of the eye.

29. A method in accordance with claim 28, wherein the transmembrane mucin is classified as one of a MUC1 mucin and MUC4 mucin.

30. A method in accordance with claim 28, wherein the transmembrane mucin is classified as MUC1 mucin.

31. A method in accordance with claim 28, further comprising:

deriving the transmembrane mucin from mammalian milk or a milk byproduct in the form of MUC1 mucin.

32. A method in accordance with claim 31, wherein deriving the transmembrane mucin includes:

processing the mammalian milk or milk byproduct to remove at least one of sugars, carbohydrates, salts, proteins, and lipids to recover a purified transmembrane mucin.

* * * * *

UNITED STATES PATENT AND TRADEMARK OFFICE
CERTIFICATE OF CORRECTION

PATENT NO.   : 6,429,194 B1
DATED        : August 6, 2002
INVENTOR(S)  : Leahy et al.

It is certified that error appears in the above-identified patent and that said Letters Patent is hereby corrected as shown below:

Title page,
Item [63], Related U.S. Application Data, delete "Continuation of application No. PCT/US01/19625, filed on Jun. 18, 2001, and a continuation-in-part of application No. 09/829,405 filed on Apr. 9, 2001, which is a continuation of application No. 09/598,089, filed on Jun. 21, 2000, now Pat. No. 6,248,360, application No. 09/888,114, which is a"

Item [60], Related U.S. Application Data, delete "Provisional application No. 60/283,976, filed on Apr. 16, 2001, and"

Signed and Sealed this

Twenty-eighth Day of September, 2004

JON W. DUDAS
*Director of the United States Patent and Trademark Office*

UNITED STATES PATENT AND TRADEMARK OFFICE
Certificate

Patent No. 6,429,194 B1                                                                      Patented: August 6, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Charles D. Leahy, Concord, MA (US); Edward J. Ellis, Lynnfield, MA (US); Jeanne Y. Ellis, Lynnfield, MA (US); Russell J. Stewart, Ph. D., Salt Lake City, UT (US); Chi-Hu Ho, Farmington, UT (US).

Signed and Sealed this Fourth Day of December 2007.

<div align="right">

WILLIAM R. DIXON, JR.
*Special Program Examiner*
Technology Center 1600

</div>